(12) United States Patent
Mitamura (10) Patent No.: US 10,412,271 B2
(45) Date of Patent: Sep. 10, 2019

(54) IMAGE PROCESSING DEVICE, MEDICAL OBSERVATION SYSTEM, AND NON-TRANSITORY COMPUTER READABLE MEDIUM STORING IMAGE PROCESSING PROGRAM

(71) Applicant: OLYMPUS CORPORATION, Tokyo (JP)

(72) Inventor: Motohiro Mitamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/806,866

(22) Filed: Nov. 8, 2017

(65) Prior Publication Data

US 2018/0069988 A1 Mar. 8, 2018

Related U.S. Application Data

(63) Continuation of application No. PCT/JP2015/064920, filed on May 25, 2015.

(51) Int. Cl.
*A61B 1/05* (2006.01)
*H04N 5/225* (2006.01)
(Continued)

(52) U.S. Cl.
CPC ....... *H04N 1/6075* (2013.01); *A61B 1/00009* (2013.01); *A61B 1/05* (2013.01);
(Continued)

(58) Field of Classification Search
CPC ........ H04N 1/62; H04N 1/628; H04N 1/6027; H04N 1/60; H04N 1/6075; H04N 1/56;
(Continued)

(56) References Cited

U.S. PATENT DOCUMENTS 4,819,077 A 4/1989 Kikuchi et al.
2002/0175993 A1 11/2002 Ueno et al.
(Continued)

FOREIGN PATENT DOCUMENTS

EP 1258221 A2 11/2002
EP 2875775 A1 5/2015
(Continued)

OTHER PUBLICATIONS

International Search Report dated Aug. 25, 2015 in PCT/JP2015/064920.

*Primary Examiner* — Jared Walker
*Assistant Examiner* — Samuel D Fereja
(74) *Attorney, Agent, or Firm* — Scully, Scott, Murphy & Presser, P.C.

(57) ABSTRACT

An image processing device including a hue acquiring unit and a lightness acquiring unit that respectively acquire hue information and lightness information of each pixel from an original color image, a color-component selecting unit that selects a color component associated with a hue range, of a plurality of hue ranges, to which the hue information of each pixel belongs as a conversion-target color component of the pixel, and a color-converted-image generating unit that generates a color-converted image in which a gradation value based on the lightness information acquired by the lightness acquiring unit is applied to the conversion-target color component selected by the color-component selecting unit from the color components of the pixels.

4 Claims, 11 Drawing Sheets

(51) Int. Cl.
*H04N 1/60* (2006.01)
*A61B 1/00* (2006.01)
*A61B 1/06* (2006.01)
*A61B 1/07* (2006.01)
*G02B 23/24* (2006.01)

(52) U.S. Cl.
CPC .............. *A61B 1/0669* (2013.01); *A61B 1/07* (2013.01); *G02B 23/2423* (2013.01); *G02B 23/2469* (2013.01); *G02B 23/2484* (2013.01); *H04N 5/2256* (2013.01); *H04N 2005/2255* (2013.01)

(58) Field of Classification Search
CPC .......... H04N 9/643; H04N 1/58; H04N 9/045; H04N 1/46; H04N 1/603; H04N 1/6055; H04N 1/6058; H04N 1/6086; H04N 2005/2255; H04N 5/2256; H04N 7/18; H04N 1/4072; H04N 1/6008; H04N 1/6019; H04N 1/6052; H04N 1/6088; H04N 2201/0094; H04N 5/232; H04N 5/23219; H04N 5/23245; H04N 9/646; H04N 9/68; H04N 13/133; H04N 13/15; H04N 17/002; H04N 1/6002; H04N 1/6005; H04N 1/6041; H04N 1/6047; H04N 1/6061; H04N 1/6072; H04N 1/6077; H04N 1/622; H04N 2201/0082; H04N 2209/046; H04N 5/23229; H04N 5/23293; H04N 5/2354; H04N 5/272; H04N 5/332; H04N 5/357; H04N 9/09; H04N 9/67; H04N 9/69; H04N 9/74; G06T 2207/10024; G06T 11/001; G06T 2207/10068; G06T 7/0012; G06T 5/009; G06T 7/90; G06T 2207/10008; G06T 2207/30096; G06T 5/008; G06T 5/40; G06T 2207/30092; G06T 2207/30201; G06T 5/002; G06T 5/007; G06T 1/00; G06T 2207/10016

See application file for complete search history.

(56) References Cited

U.S. PATENT DOCUMENTS

| | | | |
|---|---|---|---|
| 2010/0208047 A1* | 8/2010 | Kitamura | A61B 1/041 348/65 |
| 2015/0042774 A1* | 2/2015 | Sugano | H04N 5/2256 348/68 |
| 2015/0181185 A1 | 6/2015 | Ikemoto et al. | |
| 2015/0193929 A1* | 7/2015 | Ikemoto | A61B 1/00009 382/128 |
| 2018/0153384 A1* | 6/2018 | Ikemoto | A61B 1/00 |

FOREIGN PATENT DOCUMENTS

| | | |
|---|---|---|
| JP | S62266030 A | 11/1987 |
| JP | 2003126015 A | 5/2003 |
| JP | 2013094562 A | 5/2013 |
| JP | 2014018333 A | 2/2014 |

* cited by examiner

IMAGE PROCESSING DEVICE, MEDICAL OBSERVATION SYSTEM, AND NON-TRANSITORY COMPUTER READABLE MEDIUM STORING IMAGE PROCESSING PROGRAM

CROSS-REFERENCE TO RELATED APPLICATIONS

This is a continuation of International Application PCT/JP2015/064920, with an international filing date of May 25, 2015, which is hereby incorporated by reference herein in its entirety.

TECHNICAL FIELD

The present invention relates to an image processing device, a medical observation system, and a non-transitory computer readable medium storing an image processing program.

BACKGROUND ART

A known auxiliary diagnostic device for an endoscope enhances the distinguishability of a subject within an endoscopic image by converting color information of each pixel of an endoscopic image from the RGB format into the HSV format and encoding the color information based on an obtained hue value, chroma/saturation/colorfulness value, and brightness/lightness value (for example, see Patent Literature 1).

CITATION LIST

Patent Literature

{PTL 1}
Japanese Unexamined Patent Application, Publication No. 2013-094562

SUMMARY OF INVENTION

A first aspect of the present invention provides an image processing device including a hue acquiring unit that acquires hue information of each pixel from an original color image received from an external device, a lightness acquiring unit that acquires lightness information of each pixel from the original image, a color-component selecting unit that selects a conversion-target color component of each pixel of the original image from a plurality of preset color components based on the hue information, and a color-converted-image generating unit that generates a color-converted image by allocating the lightness information of each pixel of the original image to the conversion-target color component selected by the color-component selecting unit. The color-component selecting unit selects the conversion-target color component associated with a hue range to which the hue information of each pixel belongs, the hue range being included in a plurality of hue ranges obtained by dividing hues based on a hue threshold value. The color-converted-image generating unit generates the color-converted image by applying a gradation value based on the lightness information acquired by the lightness acquiring unit to each pixel corresponding to the selected conversion-target color component in the color-converted image.

A second aspect of the present invention provides a medical observation system including an observation device that acquires a color biological image by photographing a biological organism and the aforementioned image processing device that receives the biological image as the original image from the observation device.

A third aspect of the present invention provides an image processing program causing a computer to execute a process including a hue acquiring step for acquiring hue information of each pixel from an original color image, a lightness acquiring step for acquiring lightness information of each pixel from the original image, a color-component selecting step for selecting a conversion-target color component of each pixel of the original image from a plurality of preset color components based on the hue information, and a color-converted-image generating step for generating a color-converted image by allocating the lightness information of each pixel of the original image to the conversion-target color component selected in the color-component selecting step. The color-component selecting step includes selecting the conversion-target color component associated with a hue range to which the hue information of each pixel belongs, the hue range being included in a plurality of hue ranges obtained by dividing hues based on a hue threshold value. The color-converted-image generating step includes generating the color-converted image by applying a gradation value based on the lightness information acquired in the lightness acquiring step to each pixel corresponding to the selected conversion-target color component in the color-converted image.

DESCRIPTION OF EMBODIMENTS

First Embodiment

An image processing device 1 and a medical observation system 100 equipped with the image processing device 1 according to a first embodiment of the present invention will be described below with reference to FIGS. 1 to 7.

Figure 1:
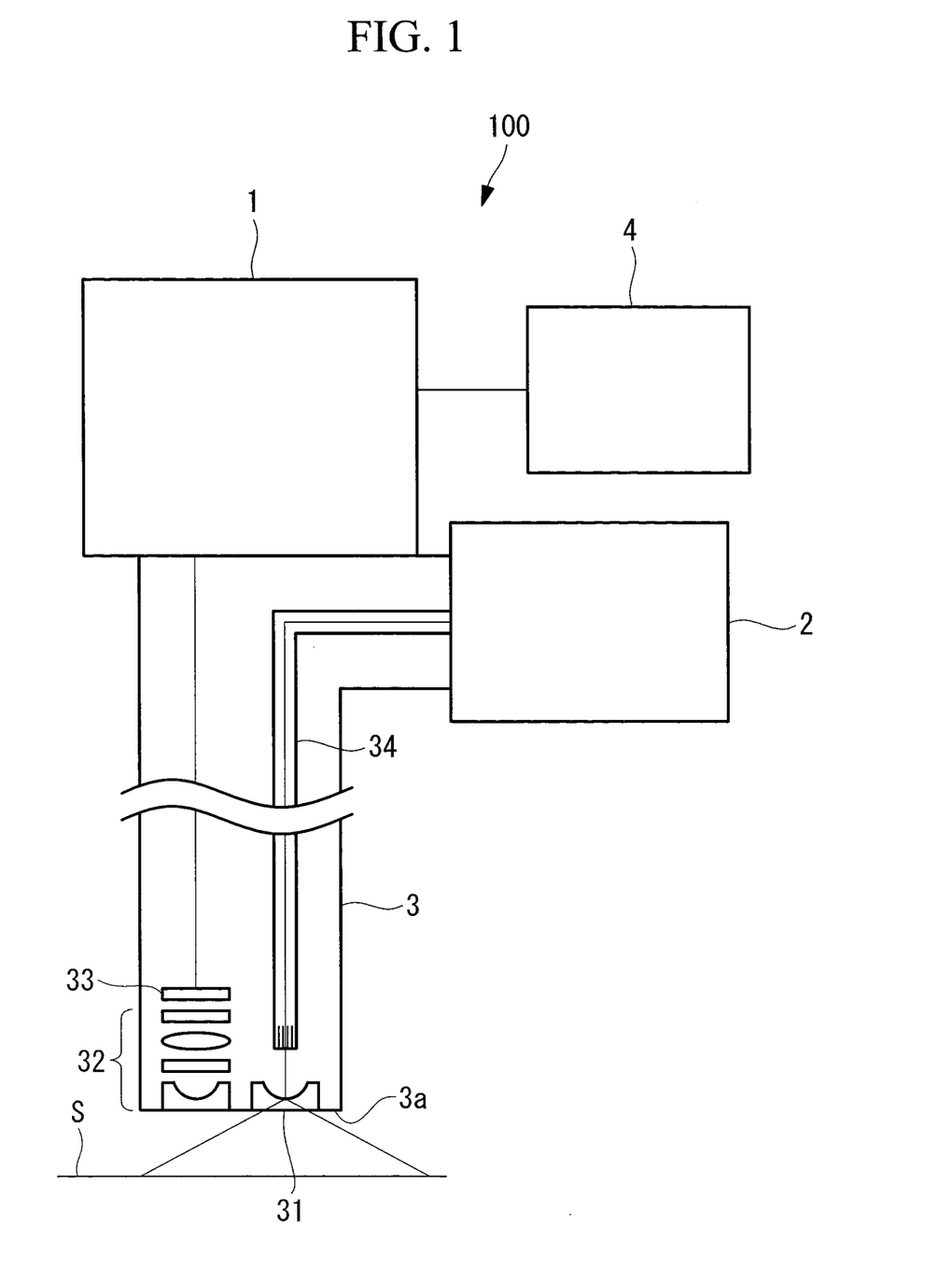
FIG. 1 illustrates the overall configuration of a medical observation system according to a first embodiment of the present invention.

As shown in FIG. 1, the medical observation system 100 according to this embodiment includes a light source 2 that outputs illumination light, an endoscope (external device, observation device) 3 that is inserted into a biological organism so as to be used for observing the inside of the biological organism, the image processing device 1 that processes a biological image acquired by the endoscope 3, and a display unit 4 that displays the image output from the image processing device 1.

The endoscope 3 includes an illumination lens 31 and an objective lens 32 that are provided at a distal end 3a thereof, and also includes an imaging element 33. The illumination lens 31 outputs the illumination light supplied from the light source 2 via a light guide 34 toward the front side of the distal end 3a. The objective lens 32 focuses light input from biological tissue S facing the distal end 3a onto an imaging surface of the imaging element 33 disposed at the base end of the objective lens 32.

The imaging element 33 is, for example, a color CCD or a color CMOS, and the pixels of an RGB full-color biological image acquired by the imaging element 33 each have color information in the RGB format. Specifically, the pixels of the biological image each have an R channel, a G channel, and a B channel, and each channel has a predetermined number of gradations (e.g., 256 gradations). The imaging element 33 transmits the acquired biological image to the image processing device 1.

Figure 2:
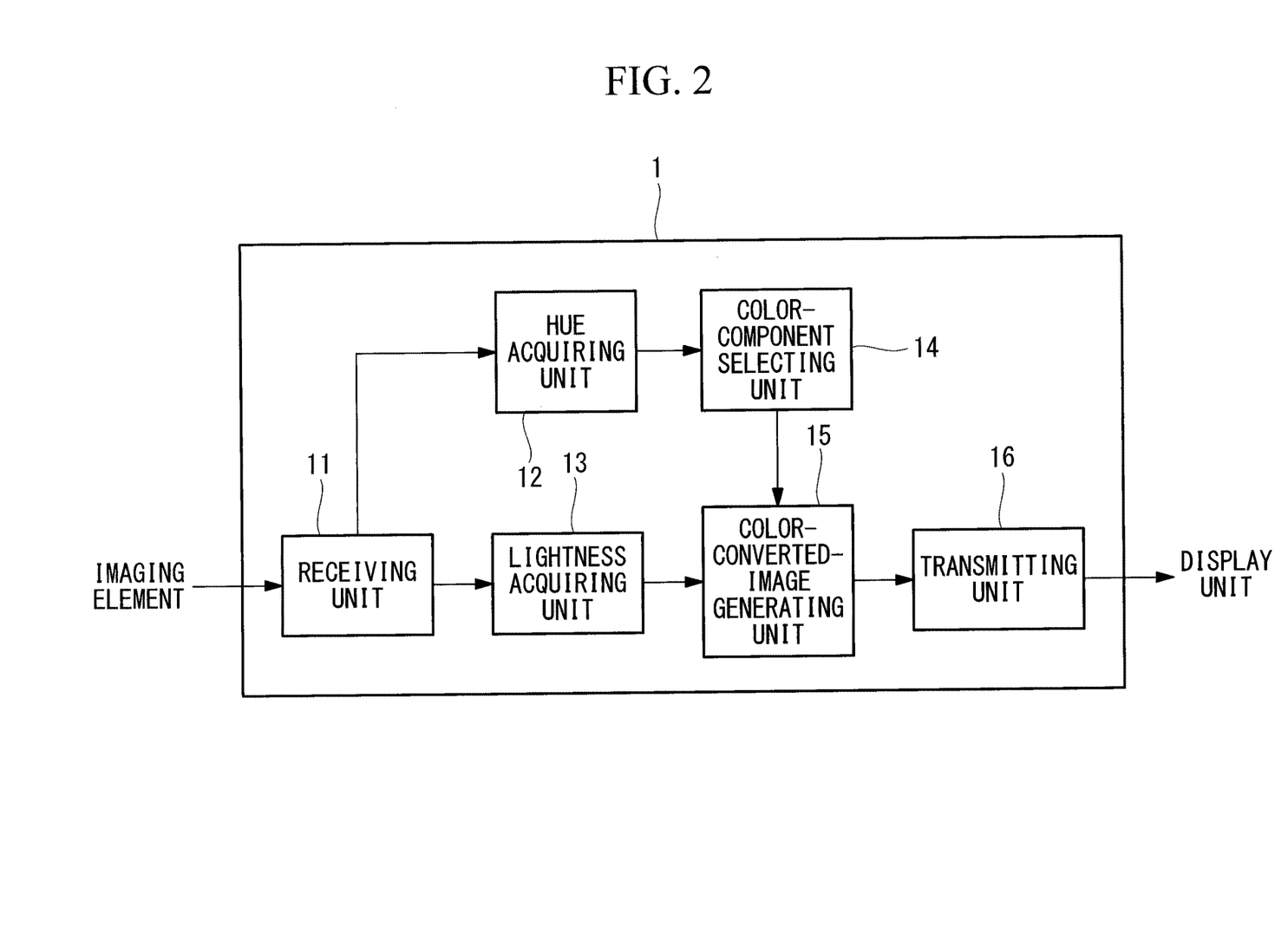
FIG. 2 is a block diagram illustrating the functions of an image processing device in the medical observation system in FIG. 1.

As shown in FIG. 2, the image processing device 1 includes a receiving unit 11 that receives the biological image (i.e., original image) from the imaging element 33, a hue acquiring unit 12 that acquires hue information of each pixel from the biological image, a lightness acquiring unit 13 that acquires lightness information of each pixel from the biological image, a color-component selecting unit 14 that selects a conversion-target color component of each pixel of the biological image from two color components, a color-converted-image generating unit 15 that converts the hue of each pixel of the biological image into the conversion-target color component so as to generate a color-converted image, and a transmitting unit 16 that transmits the color-converted image to the display unit 4.

The image processing device 1 is, for example, a general-purpose computer and includes a central processing unit (CPU), a main storage unit, such as a RAM, and an auxiliary storage unit. The auxiliary storage unit is a non-transitory computer readable storage medium that stores an image processing program therein. The CPU loads the image processing program from the auxiliary storage unit to the main storage unit and executes the image processing program so as to realize the functions of the hue acquiring unit 12, the lightness acquiring unit 13, the color-component selecting unit 14, and the color-converted-image generating unit 15. Alternatively, the image processing device 1 may include dedicated hardware (ASIC) that executes processes, which will be described later, to be performed by the units 12, 13, 14, and 15.

The hue acquiring unit 12 converts the color information of each pixel of the biological image received by the receiving unit 11 from the RGB format into color space coordinates constituted of a cylindrical coordinate system including the hue, chroma, and lightness, thereby obtaining a hue value of each pixel. The hue acquiring unit 12 transmits the obtained hue values of all of the pixels to the color-component selecting unit 14.

The lightness acquiring unit 13 converts the color information of each pixel of the biological image received by the receiving unit 11 from the RGB format into the aforementioned color space coordinates including the hue, chroma, and lightness, thereby obtaining a lightness value of each pixel. The lightness acquiring unit 13 transmits the obtained lightness values of all of the pixels to the color-converted-image generating unit 15.

Figure 3:
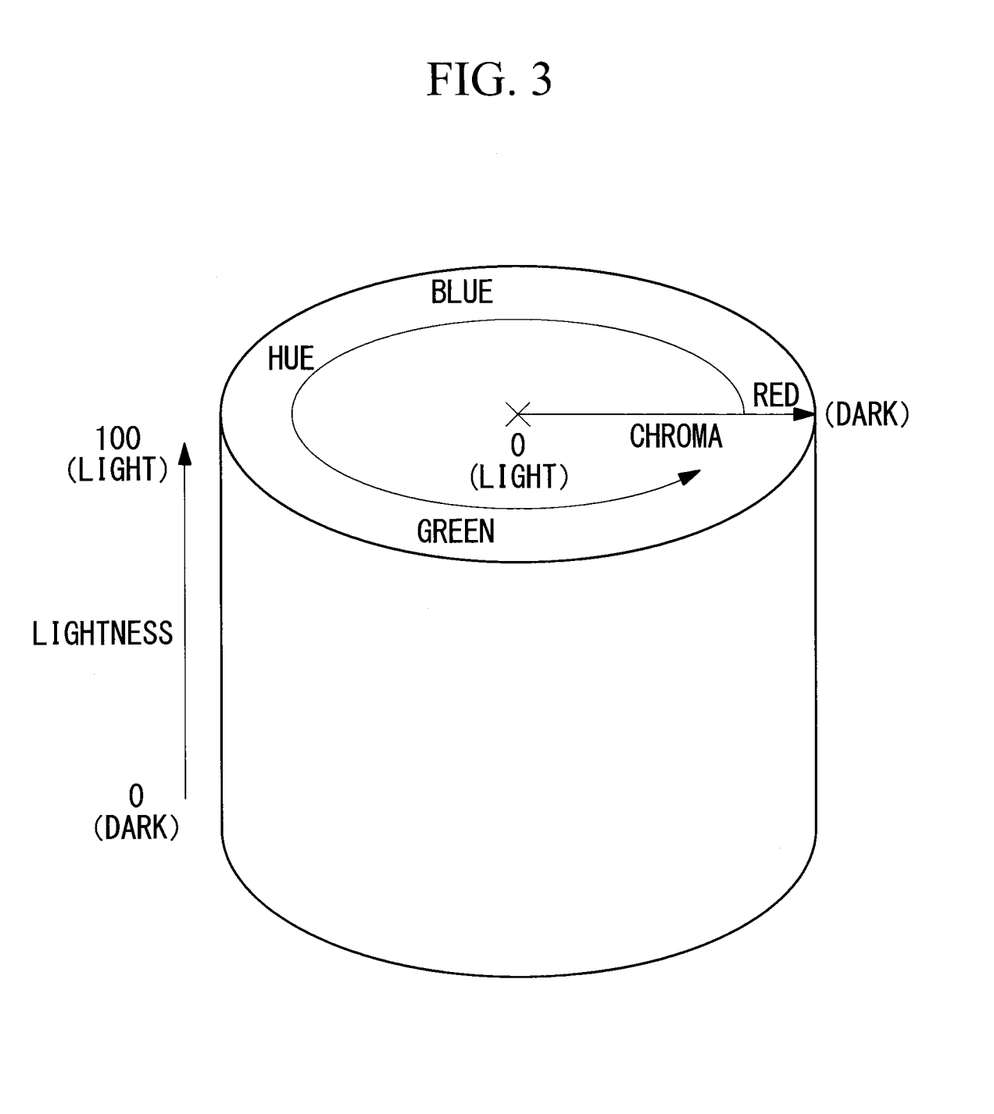
FIG. 3 illustrates a color space constituted of hue, chroma, and lightness.

FIG. 3 illustrates a cylindrical space expressing the hue-chroma-lightness color space. In this color space, the color of each pixel includes a hue value, a lightness value, and a chroma value, and the color of one pixel is expressed as the position of a single point within the color space. A hue value corresponds to an angle about the central axis of the cylindrical space and ranges between 0 inclusive and 360 exclusive. A lightness value corresponds to a height along the central axis of the cylindrical space and ranges between 0 and 100 inclusive. A chroma value corresponds to a distance from the central axis of the cylindrical space in the radial direction and ranges between 0 to 100.

Figure 4:
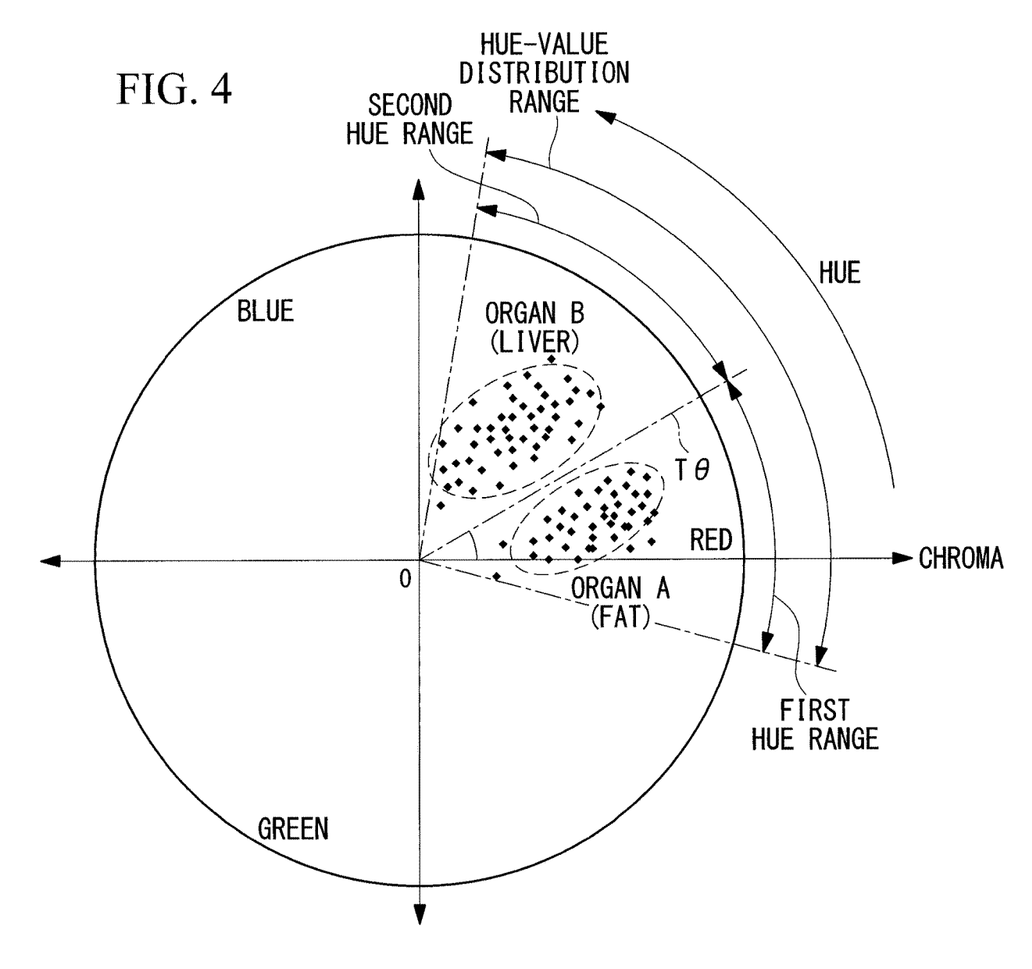
FIG. 4 illustrates an example of the distribution of colors of a biological image in a hue-chroma plane.
Figure 5:
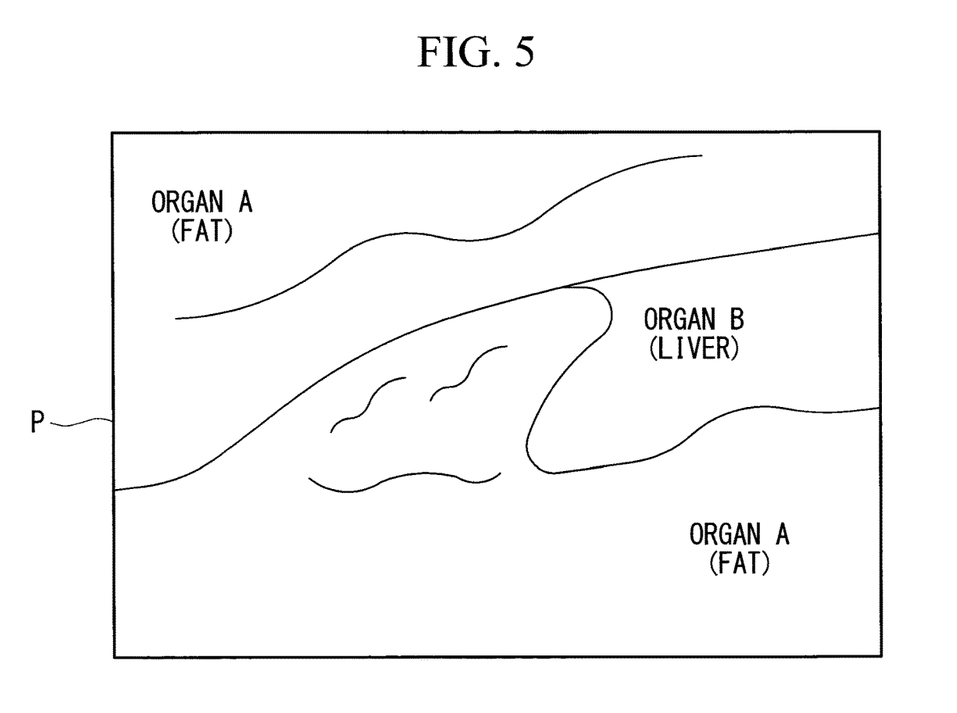
FIG. 5 illustrates an example of the biological image.

A hue-chroma plane of the biological image in the color space will now be discussed. Photographed tissue and organ (these will simply be referred to as "organs" hereinafter) in the biological image both have a red-based color. Therefore, as shown in FIG. 4, the hue values acquired by the receiving unit 11 are distributed limitedly within a partial range of the red-based color. However, the hue varies from organ to organ. For example, fat tissue has a yellow-tinged red color, and the liver has a purple-tinged red color. Therefore, as shown in FIG. 5, in a case where two kinds of organs A and B are included within a biological image P, a hue value of pixels corresponding to the organ A and a hue value of pixels corresponding to the organ B are distributed in different regions in the hue-chroma plane.

The color-component selecting unit 14 has a predetermined hue threshold value Tθ for the hue values. The hue threshold value Tθ is a value corresponding to the boundary between the region where the hue value of the pixels corresponding to the organ A is distributed and the region where the hue value of the pixels corresponding to the organ B is distributed within the hue-chroma plane. Therefore, based on the hue threshold value Tθ, the range in which the hue values of the biological image P are distributed is divided into a first hue range in which the hue values of the pixels corresponding to the organ A are distributed and a second hue range in which the hue values of the pixels corresponding to the organ B are distributed. For example, the hue threshold value Tθ is set by measuring a boundary value between the distribution regions of the hue values of the pixels corresponding to the organs A and B by using a preliminarily-acquired biological image P.

In this embodiment, it is assumed that the subject is biological tissue having a red-based color and the hue values are distributed limitedly within the red-based-color region. Therefore, based on a single hue threshold value Tθ, the hue values of all of the pixels can be reliably classified either into the first hue range or the second hue range. However, if the subject has various hues and the hue values are distributed over a wide range, a plurality of hue threshold values may be set such that a lower limit value and an upper limit value of each hue range are clearly defined.

The color-component selecting unit 14 stores green (G) as a conversion-target color component of the first hue range and stores blue (B) as a conversion-target color component of the second hue range. The color-component selecting unit 14 determines whether each pixel hue value received from the hue acquiring unit 12 belongs to the first hue range or the second hue range, selects G as a conversion-target color component of a pixel with a hue value belonging to the first hue range, and selects B as a conversion-target color component of a pixel with a hue value belonging to the second hue range.

A color-converted image is a bicolor image expressed using two hues, G and B. Each pixel of a color-converted image has a G channel and a B channel, each having a predetermined number of gradations (e.g., 256 gradations). The color-converted-image generating unit 15 receives a lightness value of each pixel from the lightness acquiring unit 13 and converts the received lightness value into a value in the predetermined number of gradations of the color-converted image. Consequently, a value based on the lightness value in the original image is obtained as a gradation value of each pixel of the color-converted image.

Figure 6:
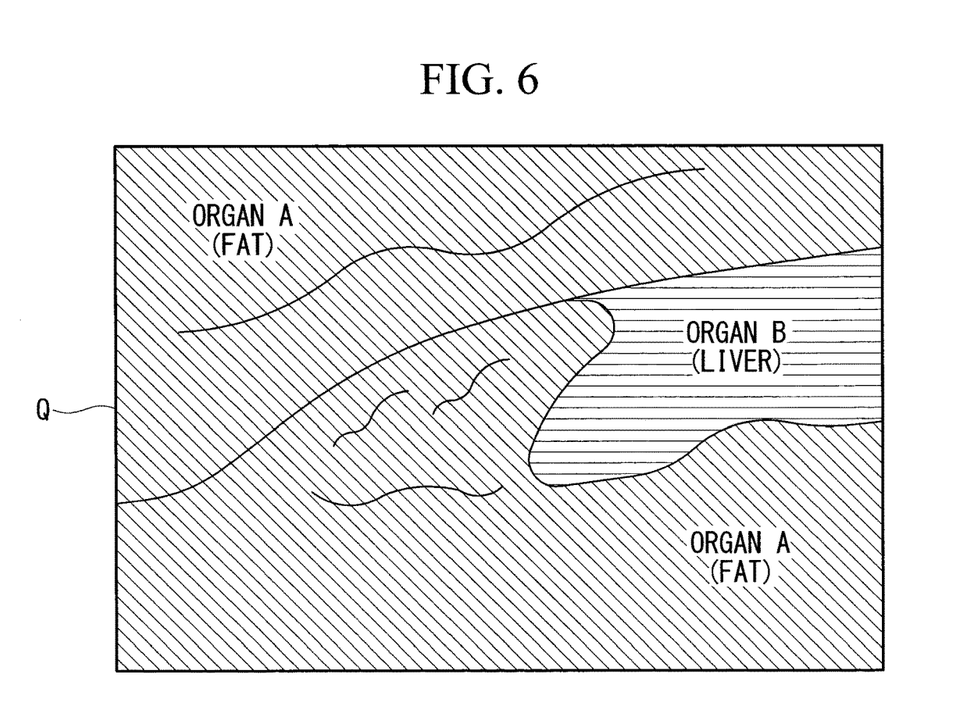
FIG. 6 illustrates an example of a color-converted image generated from the biological image in FIG. 5.

Subsequently, the color-converted-image generating unit 15 sets the obtained gradation value to a gradation value of a color-component channel selected by the color-component selecting unit 14 from between the G channel and the B channel of each pixel of the color-converted image. For example, the lightness value of a pixel having a hue value belonging to the first hue range in the biological image P is converted into a gradation value in the G channel of a pixel at the same position within the color-converted image. Thus, as shown in FIG. 6, the color-converted-image generating unit 15 generates a color-converted image Q in which the region of the organ A is displayed in green and the region of the organ B is displayed in blue. In FIG. 6, the difference in the directions of hatching indicates the difference in hues. The generated color-converted image Q is transmitted from the transmitting unit 16 to the display unit 4 so as to be displayed on the display unit 4.

Next, the operation of the image processing device 1 and the medical observation system 100 having the above-described configuration will be described.

In order to observe the inside of a biological organism by using the medical observation system 100 according to this embodiment, the endoscope 3 is inserted into the biological organism, the distal end 3a is disposed facing the biological tissue S, and illumination light is radiated onto the biological tissue S from the illumination lens 31 at the distal end 3a. The illumination light reflected at the surface of the biological tissue S is focused onto the imaging surface of the imaging element 33 by the objective lens 32, so that a biological image P is acquired by the imaging element 33. The acquired biological image P is transmitted from the endoscope 3 to the image processing device 1.

Figure 7:
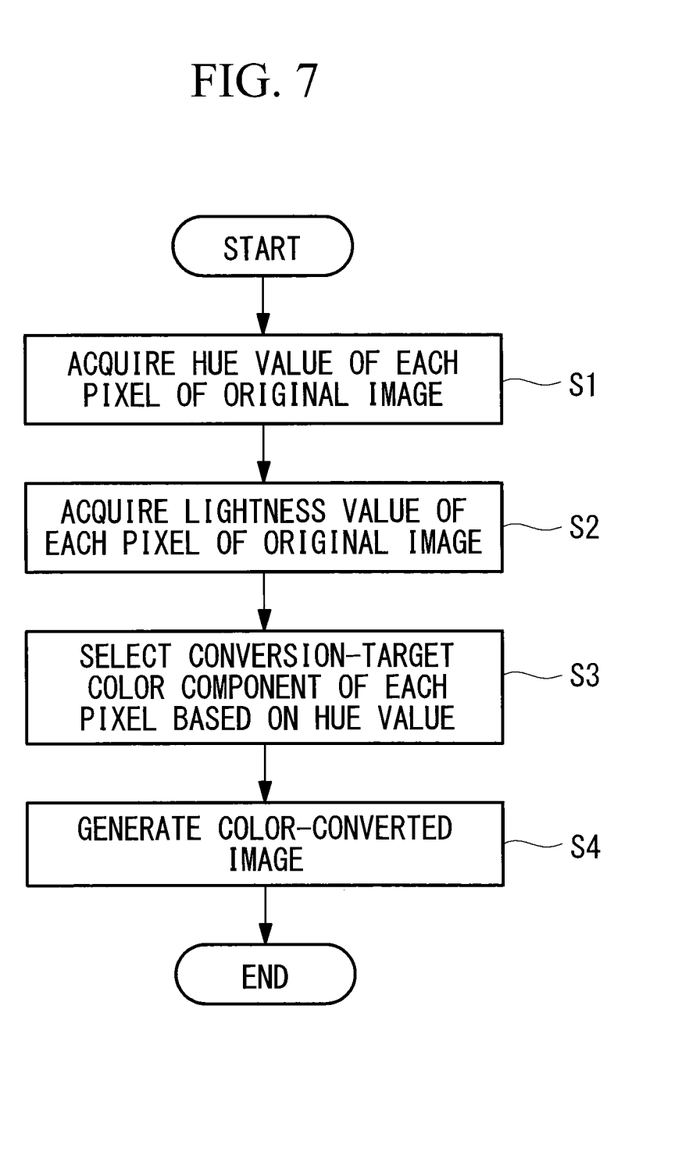
FIG. 7 is a flowchart illustrating a process executed by the image processing device in FIG. 1.

FIG. 7 illustrates a process executed by the image processing device 1.

When the biological image P is input to the image processing device 1 via the receiving unit 11, the color information of each pixel of the biological image P is converted from the RGB format into the hue-chroma-lightness color space coordinates, so that a hue value is acquired by the hue acquiring unit 12 (hue acquiring step S1) and a lightness value is acquired by the lightness acquiring unit 13 (lightness acquiring step S2). Then, the color-component selecting unit 14 selects a conversion-target color component of each pixel of the biological image P from G and B based on the hue value of the pixel (color-component selecting step S3). Subsequently, the color-converted-image generating unit 15 generates a color-converted image Q in which the lightness value of each pixel of the biological image P is set as the gradation value of the channel of the same color component as the color component selected by the color-component selecting unit 14 (color-converted-image generating step S4).

In this case, a plurality of kinds of organs inside the biological organism have similar colors. Therefore, in a normal color biological image P, it is difficult to distinguish the plurality of kinds of organs from one another. However, because organs have different hues, the plurality of kinds of organs can be distinguished from one another based on hue values. In this embodiment, it is determined which of the plurality of kinds of organs each pixel corresponds to based on the hue value of the pixel acquired from the biological image P, and the hue of the pixel is converted into a hue associated with each kind of organ. Thus, a color-converted image Q in which the organs are displayed with different hues in accordance with the kinds of organs is obtained. This is advantageous in that an observer can perform the observation while readily distinguishing the plurality of kinds of organs from one another in the color-converted image Q.

Furthermore, when the color information of each pixel of the biological image P is converted from the RGB format into the hue-chroma-lightness color space coordinates, morphological information of the biological tissue S included in the biological image P mainly remains in the lightness from among the hue, chroma, and lightness. Therefore, by setting the gradation value of each pixel of the color-converted image Q to a value based on the lightness value in the biological image P, the morphological information of the biological tissue S in the biological image P can be maintained. This is advantageous in that the morphology of the biological tissue S can also be observed by using the color-converted image Q.

Second Embodiment

Next, an image processing device 10 and a medical observation system equipped with the image processing device 10 according to a second embodiment of the present invention will be described with reference to FIGS. 8 to 12. In this embodiment, components similar to those in the first embodiment will be given the same reference signs, and descriptions thereof will be omitted.

Figure 8:
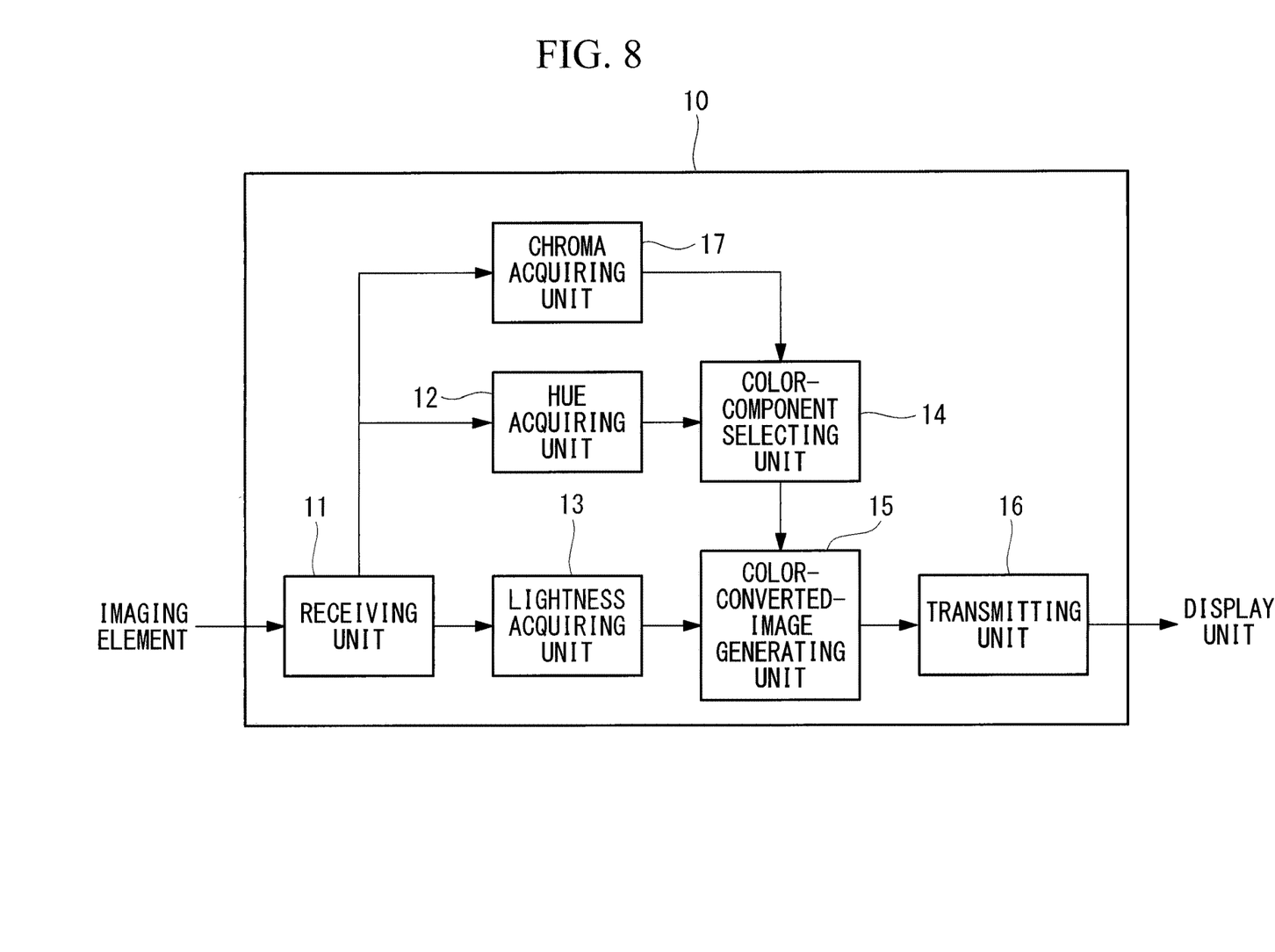
FIG. 8 is a block diagram illustrating the functions of an image processing device in a medical observation system according to a second embodiment of the present invention.

The medical observation system according to this embodiment includes the image processing device 10 in FIG. 8 in place of the image processing device 1 in FIG. 2.

The image processing device 10 further includes a chroma acquiring unit 17 that acquires a chroma value of each pixel from the biological image P. The chroma acquiring unit 17 converts the color information of each pixel of the biological image P received by the receiving unit 11 from the RGB format into the hue-chroma-lightness color space coordinates, thereby obtaining a chroma value of each pixel. The chroma acquiring unit 17 transmits the obtained chroma values of all of the pixels to the color-component selecting unit 14.

Figure 9:
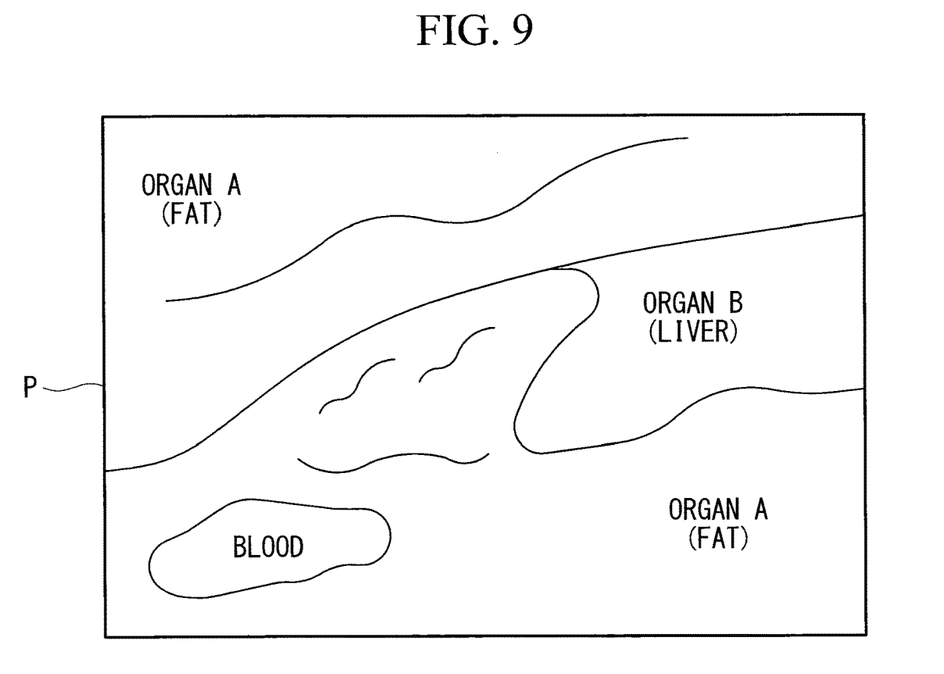
FIG. 9 illustrates another example of the biological image.
Figure 11:
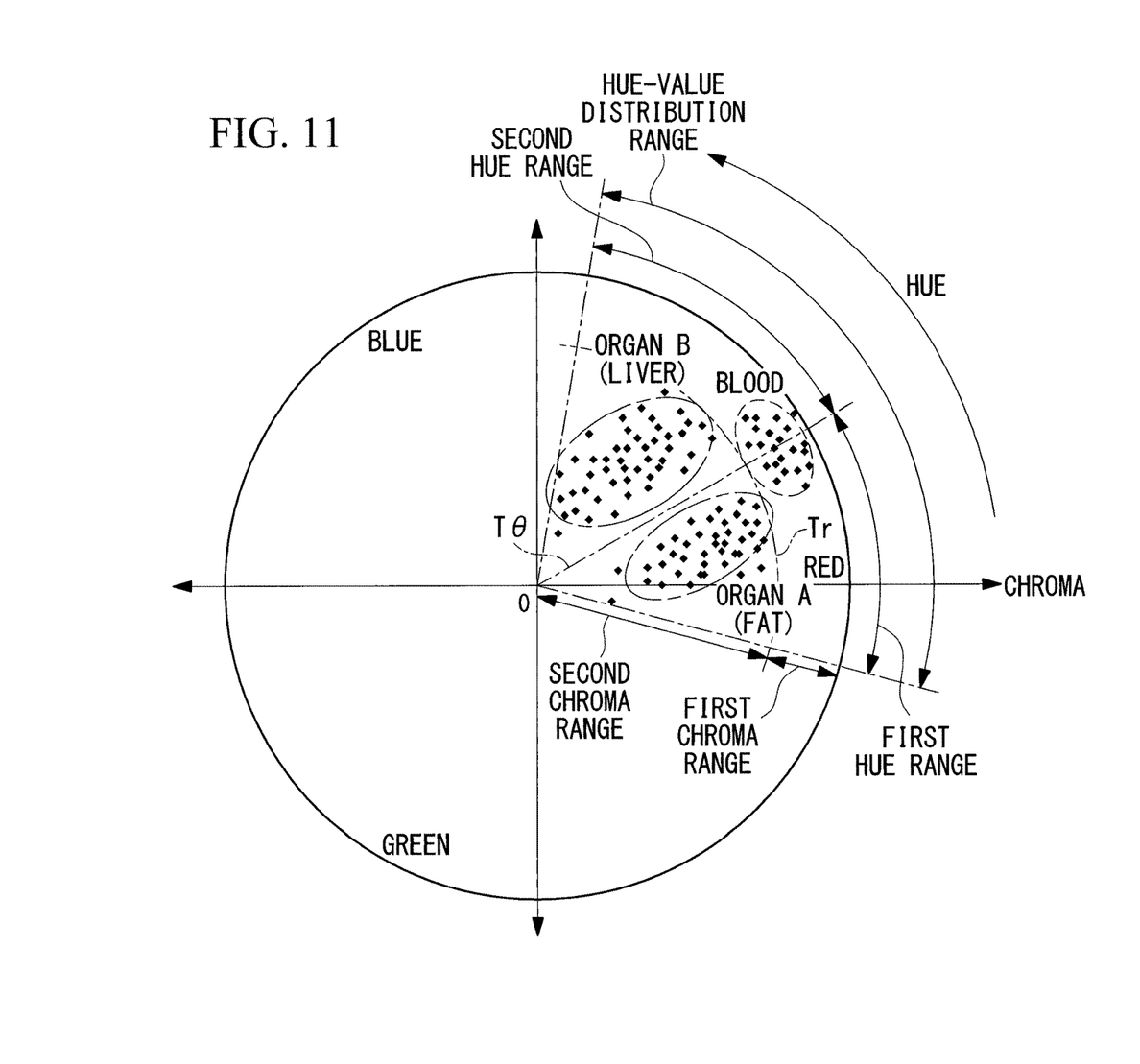
FIG. 11 illustrates another example of the distribution of colors of the biological image in the hue-chroma plane.

In a case where the biological image P includes blood in addition to the organs A and B, as shown in FIG. 9, the hue values of the pixels corresponding to the organs A and B in the hue-chroma plane are distributed lopsidedly toward the side with the lower chroma, whereas the hue value of the pixels corresponding to the blood is distributed lopsidedly toward the side with the higher chroma, as shown in FIG. 11. This is because the red color of the blood is more vivid than the red color of the organs A and B.

The color-component selecting unit 14 further has a predetermined chroma threshold value Tr for the chroma value. The chroma threshold value Tr is a value corresponding to the boundary between the region where the chroma values of the pixels corresponding to the blood are distributed and the region where the chroma values of the pixels corresponding to the organs A and B are distributed within the hue-chroma plane. Therefore, based on the chroma threshold value Tr, the range in which the chroma values of the biological image P are distributed is divided into a first chroma range in which the chroma values of the pixels corresponding to the blood are distributed and a second chroma range in which the chroma values of the pixels corresponding to the organs A and B are distributed. For example, the chroma threshold value Tr is set by measuring a boundary value between the distribution regions of the chroma values of the pixels corresponding to the blood and the organs A and B by using a preliminarily-acquired biological image P.

The color-component selecting unit 14 stores red (R) as a conversion-target color component of the first chroma range. The color-component selecting unit 14 first determines whether each pixel chroma value received from the hue acquiring unit 12 belongs to the first chroma range or the second chroma range, and then selects red (R) as a conversion-target color component of a pixel with a chroma value belonging to the first chroma range. Subsequently, of pixels with chroma values belonging to the second chroma range, the color-component selecting unit 14 selects G as a conversion-target color component of a pixel with a hue value belonging to the first hue range and selects B as a conversion-target color component of a pixel with a hue value belonging to the second hue range.

In this embodiment, the color-converted image Q is a tricolor image expressed using three hues, G, B, and R. Each pixel of a color-converted image has a G channel, a B channel, and an R channel, each having a predetermined number of gradations (e.g., 256 gradations). Similar to the first embodiment, the color-converted-image generating unit 15 obtains a gradation value of each pixel of the color-converted image from the lightness value in the original image.

Figure 10:
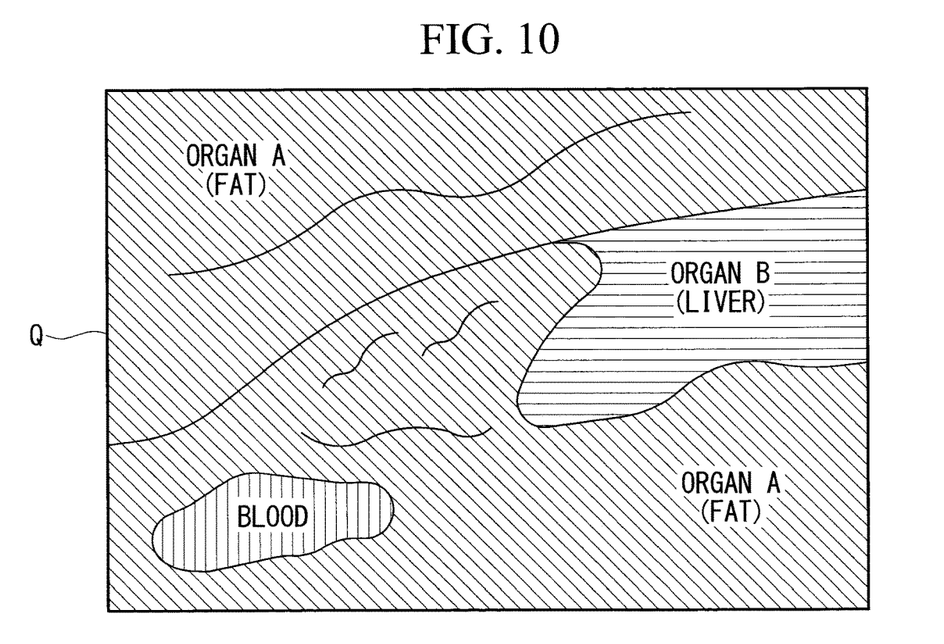
FIG. 10 illustrates an example of a color-converted image generated from the biological image in FIG. 9.

Subsequently, the color-converted-image generating unit 15 sets the obtained gradation value to a gradation value of a color-component channel selected by the color-component selecting unit 14 from among the G channel, the B channel, and the R channel of each pixel of the color-converted image. Thus, as shown in FIG. 10, the color-converted-image generating unit 15 generates a color-converted image Q in which the region of the organ A is displayed in green, the region of the organ B is displayed in blue, and the region of the blood is displayed in red. In FIG. 10, the difference in the directions of hatching indicates the difference in hues. The generated color-converted image Q is transmitted from the transmitting unit 16 to the display unit 4 so as to be displayed on the display unit 4.

Figure 12:
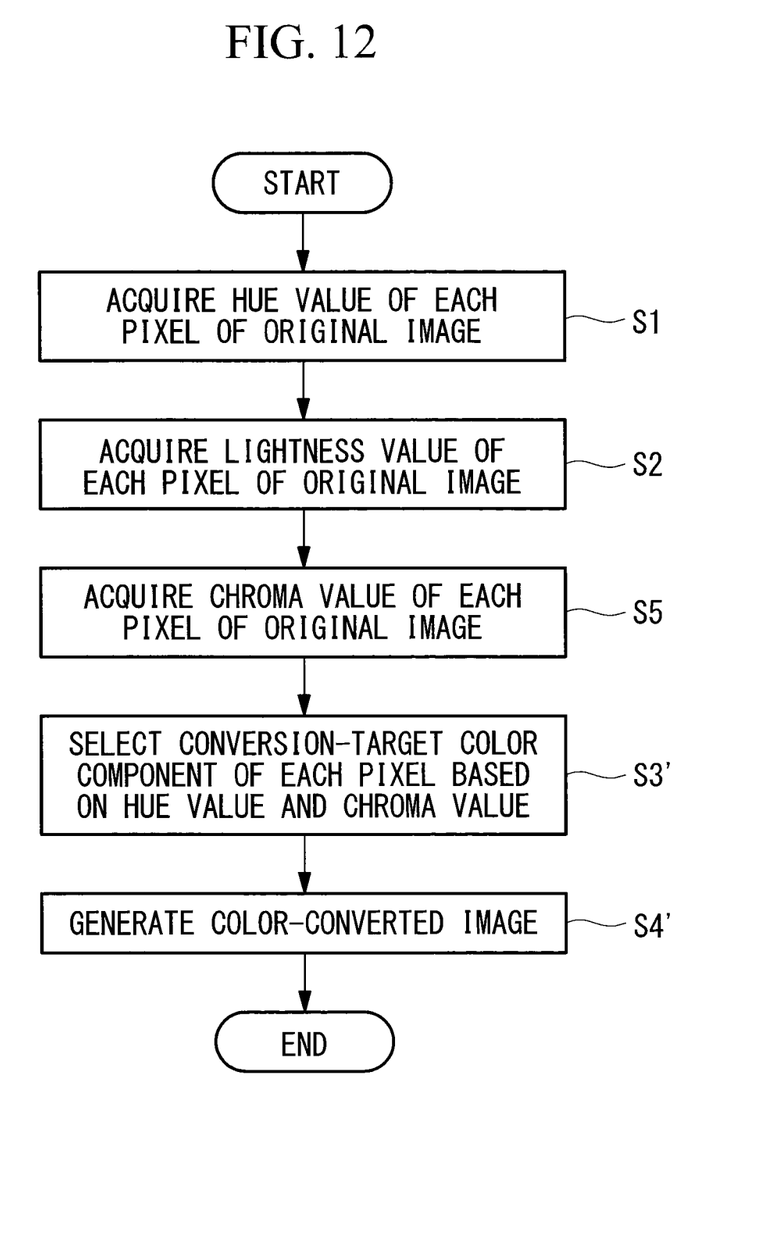
FIG. 12 is a flowchart illustrating a process executed by the image processing device in FIG. 8.

FIG. 12 illustrates a process executed by the image processing device 10.

According to the image processing device 10 and the medical observation system having the above-described configuration, when the biological image P is input to the image processing device 10 via the receiving unit 11, the color information of each pixel of the biological image P is converted from the RGB format into the hue-chroma-lightness color space coordinates, so that a hue value is acquired by the hue acquiring unit 12 (hue acquiring step S1), a lightness value is acquired by the lightness acquiring unit 13 (lightness acquiring step S2), and a chroma value is acquired by the chroma acquiring unit 17 (chroma acquiring step S5). Then, the color-component selecting unit 14 selects a conversion-target color component of each pixel of the biological image P from G, B, and R based on the chroma value and the hue value (color-component selecting step S3'). Subsequently, the color-converted-image generating unit 15 generates a color-converted image Q in which the lightness value of each pixel of the biological image P is set as the gradation value of the channel of the color component selected by the color-component selecting unit 14 (color-converted-image generating step S4').

Because the blood has a red color that is more vivid than the organs A and B, the blood can be clearly distinguished from the organs A and B based on the chroma values. According to this embodiment, it is determined which of the organs A and B and the blood each pixel corresponds to based on the chroma value of the pixel acquired from the biological image P, and the hue of the pixel corresponding to the blood is converted into a hue different from those of the pixels corresponding to the organs A and B. Thus, a color-converted image Q in which the blood and the organs A and B are displayed with different hues is obtained. This is advantageous in that an observer can perform the observation while readily distinguishing not only the plurality of kinds of organs but also the blood from one another in the color-converted image Q.

Third Embodiment

Next, an image processing device 20 and a medical observation system equipped with the image processing device 20 according to a third embodiment of the present invention will be described with reference to FIG. 13. In this embodiment, components similar to those in the first embodiment will be given the same reference signs, and descriptions thereof will be omitted.

Figure 13:
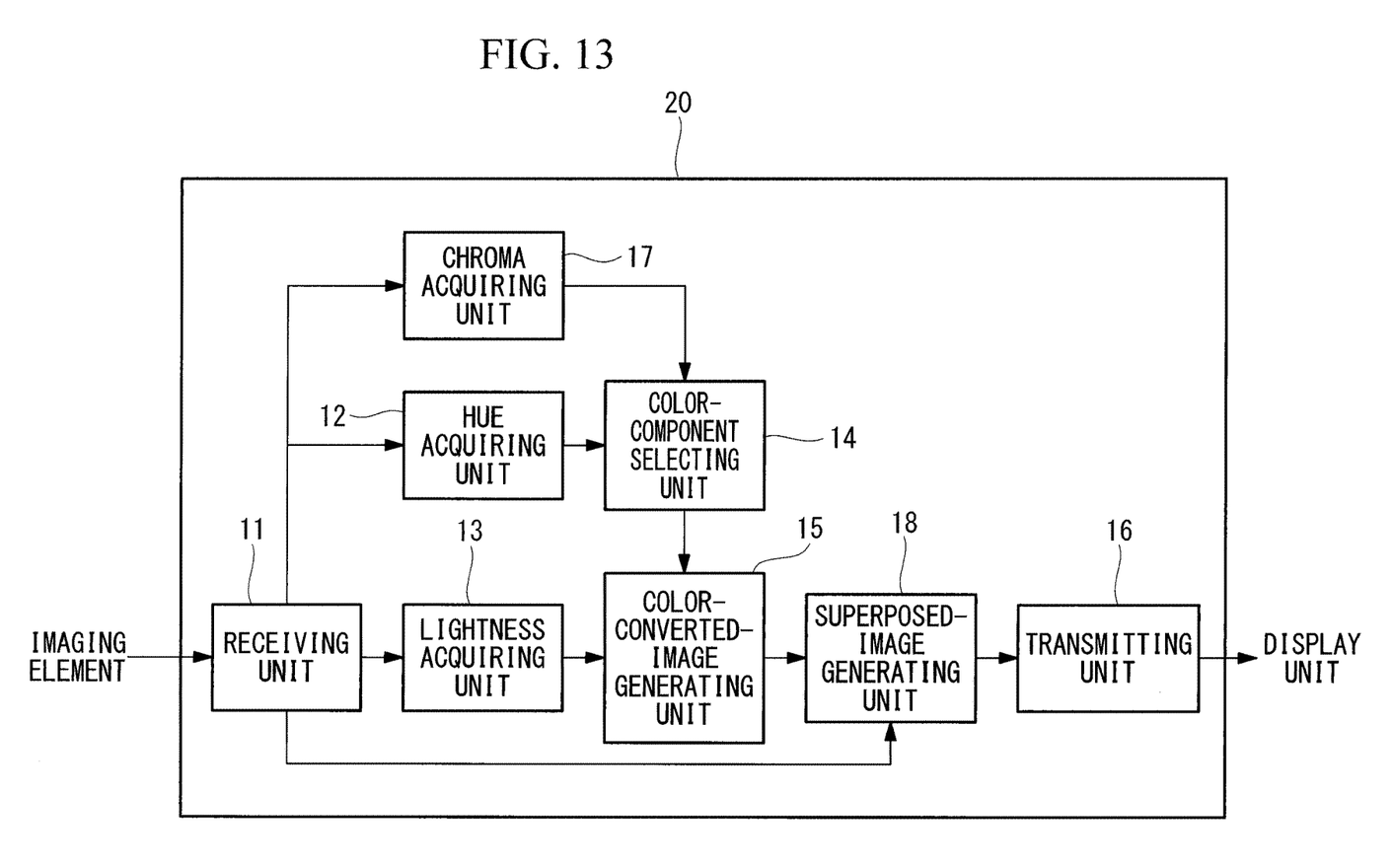
FIG. 13 is a block diagram illustrating the functions of an image processing device in a medical observation system according to a third embodiment of the present invention.

The medical observation system according to this embodiment includes the image processing device 20 in FIG. 13 in place of the image processing device 1 in FIG. 2.

The image processing device 20 further includes a superposed-image generating unit 18 that generates a superposed image by superposing the biological image P received by the receiving unit 11 and the color-converted image Q generated by the color-converted-image generating unit 15 one on top of the other. In detail, the superposed-image generating unit 18 adds together the gradation value of the R channel of each pixel of the biological image P and the gradation value of the R channel of each pixel of the color-converted image Q and sets the obtained sum as the gradation value of the R channel of each pixel of the superposed image. Similarly, the superposed-image generating unit 18 calculates the gradation values of the G channel and the B channel of each pixel of the superposed image.

In this embodiment, the superposed image generated by the superposed-image generating unit 18 is transmitted from the transmitting unit 16 to the display unit 4 so as to be displayed on the display unit 4.

According to the image processing device 20 and the medical observation system having the above-described configuration, the superposed image in which the biological image P and the color-converted image Q are superposed one on top of the other is displayed on the display unit 4. This is advantageous in that more detailed morphology of the biological tissue S can be observed by using the superposed image. Since other advantages of this embodiment are the same as those of the first and second embodiments, descriptions thereof will be omitted.

In this embodiment, the superposed-image generating unit 18 may have a weight $\alpha$ ($0<\alpha<1$) for the biological image P and a weight $\beta$ ($0<\beta<1$) for the color-converted image Q and may superpose the biological image P and the color-converted image Q one on top of the other while respectively applying the weights $\alpha$ and $\beta$ thereto. In this case, the weight $\alpha$ is set to be larger than the weight $\beta$.

In detail, the superposed-image generating unit 18 multiplies the gradation value of the R channel of each pixel of the biological image P by the weight α, multiplies the gradation value of the R channel of each pixel of the color-converted image Q by the weight β, and sets the sum of the two obtained products as the gradation value of the R channel of each pixel of the superposed image. Similarly, the superposed-image generating unit 18 calculates the gradation values of the G channel and the B channel of each pixel of the superposed image.

In the superposed image, the organ A is displayed overall in a green-tinged color, as compared with its original color, the organ B is displayed overall in a blue-tinged color, as compared with its original color, and the blood is displayed in a more vivid red color, as compared with its original color. By using the weights α and β to appropriately adjust the ratio between the gradation value derived from the biological image P and the gradation value derived from the color-converted image Q in the superposed image, the colors of the organs A and B and the blood in the superposed image are prevented from being excessively toward the conversion-target color components while maintaining the distinguishability among the organs A and B and the blood based on the conversion-target color components. This is advantageous in that the organs A and B and the blood in the superposed image can be expressed in colors closer to their original colors.

As an alternative to this embodiment in which the chroma acquiring unit 17 is provided and the color-converted-image generating unit 15 generates a tricolor image as a color-converted image Q, the chroma acquiring unit 17 may be omitted, and the color-converted-image generating unit 15 may generate a bicolor image, described in the first embodiment, as a color-converted image Q.

Furthermore, in the first to third embodiments, G or B is allocated to the pixels corresponding to the organ A or B and R is allocated to the pixels corresponding to the blood in the color-converted image Q. Alternatively, the allocation of the color components in the color-converted image Q may be changed, where appropriate.

Moreover, the conversion-target color component in the color-converted image Q is not limited to one of R, G, and B, and may be two or more thereof. For example, the gradation value of the pixels corresponding to the organ A may be distributed to two or more of the three R, G, and B channels at a predetermined ratio, so that the organ A in the color-converted image Q is displayed in an intermediate color other than the three primary colors (R, G, and B). If four or more kinds of organs are to be observed, the color-converted image may be a multicolor image expressed using four or more hues.

Although the medical observation system 100 equipped with the endoscope 3 is described in the first to third embodiments, another type of observation device different from an endoscope may be used, so long as a color biological image P can be acquired.

As a result, the above-described embodiments lead to the following aspects.

A first aspect of the present invention provides an image processing device including a hue acquiring unit that acquires hue information of each pixel from an original color image received from an external device, a lightness acquiring unit that acquires lightness information of each pixel from the original image, a color-component selecting unit that selects a conversion-target color component of each pixel of the original image from a plurality of preset color components based on the hue information, and a color-converted-image generating unit that generates a color-converted image by allocating the lightness information of each pixel of the original image to the conversion-target color component selected by the color-component selecting unit. The color-component selecting unit selects the conversion-target color component associated with a hue range to which the hue information of each pixel belongs, the hue range being included in a plurality of hue ranges obtained by dividing hues based on a hue threshold value. The color-converted-image generating unit generates the color-converted image by applying a gradation value based on the lightness information acquired by the lightness acquiring unit to each pixel corresponding to the selected conversion-target color component in the color-converted image.

According to the first aspect of the present invention, when the original image is input from the outside, the hue information of each pixel of the original image is acquired by the hue acquiring unit, the conversion-target color component of each pixel is selected by the color-component selecting unit based on the acquired hue, and the hue of each pixel is converted into a hue according to the selected conversion-target color component by the color-converted-image generating unit. Accordingly, a color-converted image in which only the conversion-target color component is used is generated from the original full-color image.

In this case, even if a plurality of kinds of subjects included in the original image have similar colors, the hue varies from subject to subject. Therefore, the hue information of pixels corresponding to one subject and the hue information of pixels corresponding to another subject belong to different hue ranges, so that the plurality of kinds of subjects are displayed with different conversion-target color components in the color-converted image. Consequently, high distinguishability of subjects can be ensured in the color-converted image.

Furthermore, morphological information of a subject within the original image mainly remains in the lightness from among three elements, namely, the hue, chroma, and lightness, constituting the color of each pixel of the original image. Therefore, by setting the gradation value of each pixel of the color-converted image to a value based on the lightness information of each pixel of the original image acquired by the lightness acquiring unit, a color-converted image in which the morphological information of the subject included in the original image is maintained can be generated.

In the first aspect, the image processing device may further include a chroma acquiring unit that acquires chroma information of each pixel from the original image. The color-component selecting unit may select the conversion-target color component associated with a chroma range to which the chroma information of each pixel belongs, the chroma range being included in a plurality of chroma ranges obtained by dividing a range in which the chroma information acquired by the chroma acquiring unit is distributed based on a predetermined chroma threshold value.

Accordingly, subjects having similar hues such that separation based on hue alone is difficult can be distinguished from each other based on the difference in chroma, and can be displayed with different hues in the color-converted image.

In the first aspect described above, the image processing device may further include a superposed-image generating unit that generates a superposed image in which the original image and the color-converted image are superposed one on top of the other.

Accordingly, a superposed image containing more distinct morphological information of the subject can be generated.

In the first aspect described above, the superposed-image generating unit may superpose the original image and the color-converted image one on top of the other while respectively applying weights thereto such that the weight for the original image is larger than the weight for the color-converted image.

Accordingly, a change in the color of the subject within the superposed image, which may be caused due to superposing of the color-converted image onto the original image, can be suppressed.

A second aspect of the present invention provides a medical observation system including an observation device that acquires a color biological image by photographing a biological organism and the aforementioned image processing device that receives the biological image as the original image from the observation device.

According to the second aspect of the present invention, a color-converted image is generated in the image processing device from the biological image acquired by the observation device. In this case, the biological image includes a plurality of kinds of tissue and organs having red-based colors. Since these plurality of kinds of tissue and organs having similar colors are displayed with different hues in the color-converted image, the plurality of kinds of tissue and organs that are difficult to distinguish from one another in the biological image can be readily distinguished from one another in the color-converted image. Moreover, the morphology of the subject can also be observed by using the color-converted image.

A third aspect of the present invention provides an image processing program causing a computer to execute a process including a hue acquiring step for acquiring hue information of each pixel from an original color image, a lightness acquiring step for acquiring lightness information of each pixel from the original image, a color-component selecting step for selecting a conversion-target color component of each pixel of the original image from a plurality of preset color components based on the hue information, and a color-converted-image generating step for generating a color-converted image by allocating the lightness information of each pixel of the original image to the conversion-target color component selected in the color-component selecting step. The color-component selecting step includes selecting the conversion-target color component associated with a hue range to which the hue information of each pixel belongs, the hue range being included in a plurality of hue ranges obtained by dividing hues based on a hue threshold value. The color-converted-image generating step includes generating the color-converted image by applying a gradation value based on the lightness information acquired in the lightness acquiring step to each pixel corresponding to the selected conversion-target color component in the color-converted image.

The present invention is advantageous in being able to provide an image in which high distinguishability of a subject is ensured while maintaining morphological information of the subject included in an original image.

REFERENCE SIGNS LIST 1, 10, 20 image processing device
2 light source
3 endoscope (external device, observation device)
4 display unit
12 hue acquiring unit
13 lightness acquiring unit
14 color-component selecting unit
15 color-converted-image generating unit
17 chroma acquiring unit
18 superposed-image generating unit
100 medical observation system
S1, S1' hue acquiring step
S2, S2' lightness acquiring step
S3, S3' color-component selecting step
S4, S4' color-converted-image generating step
S5 chroma acquiring step

The invention claimed is:

1. An image processing device comprising:
a processor comprising hardware, the processor being configured to:
acquire hue information of each pixel from an original color image received from an external device;
acquire lightness information of each pixel from the original color image;
select a conversion-target color component of each pixel of the original color image from a plurality of preset color components based on the acquired hue information;
generate a color-converted image by allocating the acquired lightness information of each pixel of the original image to the selected conversion-target color component, and
generate a superposed image in which the original image and the color-converted image are superposed one on top of the other,
wherein the selecting of the conversion-target color component selects the conversion-target color component associated with a hue range to which the hue information of each pixel belongs, the hue range being included in a plurality of hue ranges obtained by dividing hues based on a hue threshold value,
generating of the color-converted image generates the color-converted image by applying a gradation value based on the acquired lightness information to each pixel corresponding to the selected conversion-target color component in the color-converted image, and
the generating of the superimposed image superposes the original color image and the color-converted image one on top of the other while respectively applying weights thereto such that the weight for the original image is larger than the weight for the color-converted image.

2. The image processing device according to claim 1, wherein the processor is further configured to:
acquire chroma information of each pixel from the original color image,
wherein the selecting of the conversion-target color component selects the conversion-target color component associated with a chroma range to which the chroma information of each pixel belongs, the chroma range being included in a plurality of chroma ranges obtained by dividing a range in which the acquired chroma information is distributed based on a predetermined chroma threshold value.

3. A medical observation system comprising:
an observation device comprising an imaging sensor that acquires a color biological image by photographing a biological organism; and
the image processing device according to claim 1 that receives the biological image as the original color image from the observation device.

4. A non-transitory computer readable medium storing an image processing program causing a computer to execute a process comprising:

acquiring hue information of each pixel from an original color image;

acquiring lightness information of each pixel from the original color image;

selecting a conversion-target color component of each pixel of the original color image from a plurality of preset color components based on the acquired hue information;

generating a color-converted image by allocating the acquired lightness information of each pixel of the original color image to the selected conversion-target color component, and generating a superposed image in which the original image and the color-converted image are superposed one on top of the other, wherein the selecting of the conversion-target color-component comprises selecting the conversion-target color component associated with a hue range to which the hue information of each pixel belongs, the hue range being included in a plurality of hue ranges obtained by dividing hues based on a hue threshold value, generating of the color-converted image comprises generating the color-converted image by applying a gradation value based on the acquired lightness information to each pixel corresponding to the selected conversion-target color component in the color-converted image, and the generating of the superimposed image superposes the original color image and the color-converted image one on top of the other while respectively applying weights thereto such that the weight for the original image is larger than the weight for the color-converted image.

* * * * *